United States Patent [19]
Eggleton et al.

[11] 3,951,140
[45] Apr. 20, 1976

[54] ULTRASONIC THERAPY APPARATUS AND METHOD

[75] Inventors: Reginald C. Eggleton; Francis J. Fry, both of Indianapolis, Ind.

[73] Assignee: Indianapolis Center for Advanced Research, Indianapolis, Ind.

[22] Filed: Nov. 13, 1974

[21] Appl. No.: 523,268

[52] U.S. Cl. .......................... 128/24 A; 128/2.05 Z
[51] Int. Cl.² ........................ A61B 6/00; A61N 5/00
[58] Field of Search ............... 128/2 R, 2 V, 2.05 F, 128/2.05 R, 2.05 V, 2.05 Z, 2.06 A, 2.06 R, 2.1 Z, 24 A

[56] References Cited
UNITED STATES PATENTS

| | | | |
|---|---|---|---|
| 2,937,640 | 5/1960 | Bastir | 128/24 A |
| 3,144,019 | 8/1964 | Haber | 128/2.06 A |
| 3,338,235 | 8/1967 | Gordon | 128/24 A |
| 3,561,430 | 2/1971 | Filler, Jr. et al. | 128/2.05 Z |
| 3,598,110 | 8/1971 | Edmark | 128/2.06 A |
| 3,730,191 | 5/1973 | Namon | 128/2.05 F |
| 3,789,833 | 2/1974 | Bom | 128/2.05 Z |

OTHER PUBLICATIONS

1970 Annual Report of the Medical Ultrasonics Research Center, Juntendo U. School of Medicine, Hongo, Tokyo, Japan.
Yamanaka et al., "Medical Ultrasonics," Vol. 8, No. 1, pp. 86–89, 1970.
Yamanaka et al., "Medical Ultrasonics," Vol. 9, No. 1, pp. 30–32, 1970.

*Primary Examiner*—William E. Kamm
*Attorney, Agent, or Firm*—Woodard, Weikart, Emhardt & Naughton

[57] ABSTRACT

An ultrasonic apparatus is used for diagnosis and therapy of patients being treated for post-myocardial infarction. The instrument administers treatment prescribed by the physician in response to signs and symptoms continuously being monitored by the diagnostic portion of the instrument. Both the diagnosis and the treatment are non-invasive and atraumatic in nature. The diagnostic portion of the instrument is sensitive to conditions which are potentially hazardous to the patient's life, such as premature ventricular contractions, low cardiac output, and formation of secondary lesions, and initiates treatment capable of reversing these undesirable conditions. An ultrasonic transduer for producing low level ultrasound is positioned upon the chest of the patient and is acoustically coupled to the skin. The extent of the damage to the myocardium as well as the abnormal performance of the heart is reduced through the use of low level acoustical dosages applied in the manner prescribed by the physician and upon the patient's response to treatment. A computer is used to administer the treatment strategy programed into the machine which can distinguish between the various combinations of symptoms and responses of the patient to provide the prescribed optimal treatment for the particular set of circumstances and conditions which exist at any instant in time. Various non-invasive diagnostic input devices are also applied to the skin of the patient as a basis of control of the low intensity sound.

9 Claims, 2 Drawing Figures

ULTRASONIC THERAPY APPARATUS AND METHOD

BACKGROUND OF THE INVENTION

The invention is in the field of therapeutic ultrasound apparatus and methods.

Ultrasound has been used in various diagnostic procedures, including the visualization of the interior structure and valvular operation of the human heart. Ultrasound has also been used in certain therapeutic procedures, such as for muscle heating. Examples of this type of therapeutic use of ultrasound may be found in U.S. Pat. No. 3,735,756 to Richards et al and in U.S. Pat. No. 3,828,769 to Mettler. Heretofore, to applicant's knowledge, a physician-controlled treatment system has not been proposed to utilize ultrasound apparatus in the treatment of post-myocardial infarct.

Despite advances in the understanding, diagnosis, and treatment of myocardial infarction, this disease process still ranks as the number one cause of death in much of the world today. It has been only in the last decade or so that investigators have met with success in trying to understand the problems and have been able to devise treatment regimens based on adequate scientific investigation. This is evidenced by the success of coronary care units in monitoring and treating arrythmias resulting from electrical malfunctions, so that death from such malfunctions now can be nearly abolished.

More recently, efforts have been directed toward limiting the size of infarcted myocardium and enhancing the healing process. Such efforts are based on the experimental finding that in ischemically injured myocardium there is generally a central zone of irreversibly injured myocardial cells and a surrounding zone of reversibly injured cells that survive the acute episode. In ny of the occlusive processes that lead to ischemic damage, the possible role of cell swelling resulting from the ischemia recently has been recognized as a mechanism of secondary damage. When coronary blood flow is restricted, the metabolism of the myocardial cells is inhibited so that the active processes which require energy are also inhibited as soon as the energy stores are depleted. The ionic concentrations which are maintained by active transport mechanisms are upset. The intracellular osmotic pressure increases as the sodium concentration increases, and thus the cells swell. It has been suggested that the resulting edema actually may contribute to the restriction of blood flow, thus compounding the trauma to the myocardium.

Low intensity ultrasound has been used in the past in physical medicine for combatting edema and the swelling of tissues. It has been demonstrated that ultrasonic irradiation increases the permeability of synovial membranes; and it has also been found that ultrasound increases the permeability of membranes in a dialysis unit. Recent studies suggest the possible beneficial effects of low intensity ultrasound on the processes of regeneration and repair of injured tissues. For example, it has been reported that there was an increased rate of healing in wounds treated for five minutes three times per week with low intensity pulsed ultrasound. One study has shown that there is less necrosis, less fibrosis, and increased vascularization in acutely infarcted myocardium irradiated with ultrasound (810 KHz, 1 w/cm$^2$) for eight treatments during an 18-day period.

In the infarcted heart, circulation is at its lowest ebb at the very time when the demands for transport are the greatest, i.e. when degeneration of heart muscle and subsequent regeneration of scar tissue are taking place. During the height of the degenerative processes, the environment within the lesion is not conducive to the survival of normal tissue components.

Apparently, small vessels are lost during this stage inasmuch as scar tissue normally exhibits far less vascularity than normal myocardium, thus any treatment mode which favors the survival or development of circulation within the lesion contributes a most desirable factor for the repair process. Ultrasound has been shown to be capable of producing flow of interstitial fluids resulting from radiation pressure. Thus ultrasonic treatments can provide a form of circulation during the most critical stages of degeneration so that small blood vessels within the muscle can survive as well as promote the proliferation of new vascularity into the infarcted region. Swelling of cells in the vicinity of the lesion as previously noted tends to further compromise the already traumatized tissue, and it has been shown that low level ultrasound is effective in increasing the permeability of the cellular membranes with a concomitant reduction of cell volume in edematous tissue. Insofar as these benefits accrue to cells of the myocardium compromised by myocardial infarction, the trauma will be materially reversed for the patient.

SUMMARY OF THE INVENTION

One embodiment of the present invention is an apparatus for the therapeutic application of ultrasound to a subject's heart comprising ultrasound means for producing ultrasonic energy at an output, positioning means for directing the output of the ultrasound means to the heart of the subject, control means having an input responsive to signals representative of the condition of the heart for controlling the production of ultrasonic energy by the ultrasound means, monitor means for monitoring the condition of the heart, having an output dependent upon the condition of the heart, and feedback means for coupling the output of the monitor means to the input of the control means.

The system shown in FIG. 1 provides a physician-regulated automatic therapeutic, and diagnostic, apparatus for reducing the effect of post-myocardial infarct. This use of ultrasound is advantageous in the therapy period because, during healing of the damaged heart muscle, more small blood vessels will be formed in the healing area, and a less erratic heartbeat will result during this period. Further advantages include better blood and interstitial fluid flows in the heart tissue during therapy and less swelling of the heart from water absorption by the cells of the heart. Further, there is a reduction of toxins released by dying cells and an elimination of electrical reflection of the heart electrical wave by the damaged area of the heart.

It is an object of the present invention to provide an apparatus for the therapeutic application of ultrasound in the treatment of post-myocardial infarct.

It is a further object of the present invention to provide a method for the therapeutic application of ultrasound in the treatment of post-myocardial infarct.

Further objects and advantages of the present invention shall be apparent from the following detailed description and accompanying figures.

DESCRIPTION OF THE PREFERRED EMBODIMENT

Figure 1:
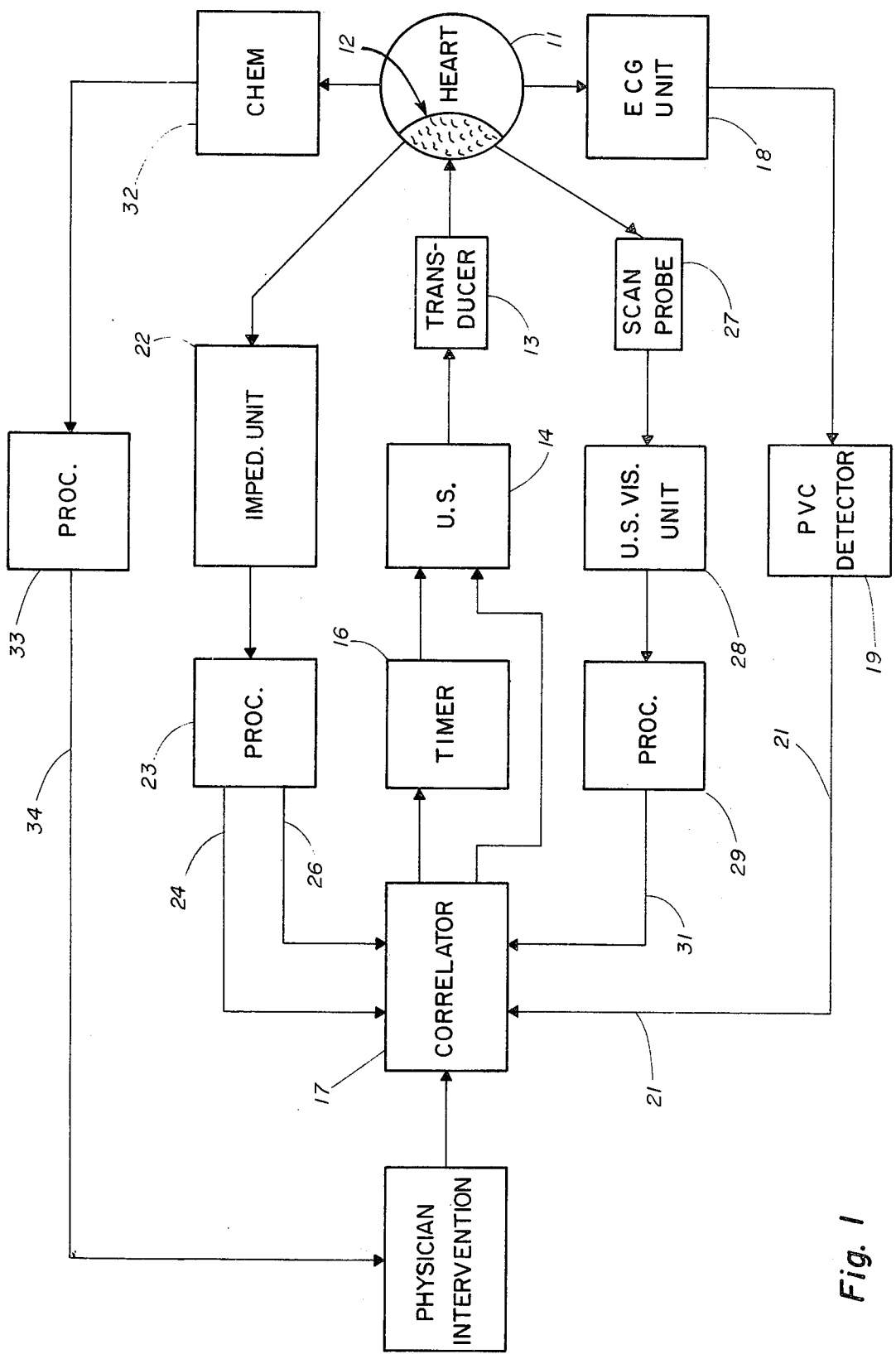
FIG. 1 is a block diagram of a therapeutic ultrasound apparatus according to the present invention.

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring in particular to FIG. 1, there is shown schematically a patient's heart 11 having an infarcted area 12. Ultrasonic energy from ultrasonic transducer 13 is coupled through an appropriate coupling medium, generally included in block 13, to the infarcted area 12 of heart 11. Transducer 13 is preferably a 1 megahertz, 3 cm. diameter, unfocused transducer, and transducer 13 is preferably mounted in a stainless steel housing which includes means for angulating the beam from transducer 13. The transducer has an output on the order of 1 w/cm$^2$ in continuous operation.

Therapeutic ultrasound unit 14 includes means for electrically energizing transducer 13 to produce the ultrasonic energy directed to heart 11. Therapeutic ultrasonic generator unit 14 is activated and controlled by timer 16 and correlator, or computer, 17 as shall be described more particularly hereinafter.

In the ultrasound heart therapy system of FIG. 1, there are also provided a plurality of monitors of the function of heart 11 to provide feedback information to correlator 17 in order to initiate appropriate physician-programed dosages of ultrasound from transducer 13 and ultrasound unit 14. An electrocardiogram unit 18 is coupled at an output to premature ventricular contraction (PVC) detector 19. PVC detector 19, such as manufactured by Wolff Industries of San Marino, Calif., provides an output at 21, such as a pulse upon the occurrence of a PVC, as decoded from the electrocardiogram unit output. This PVC pulse is coupled to correlator 17 for use as shall be described hereinafter. The output of PVC detector 19 might also comprise a signal indicative of an excess in the number of abnormalities in heartbeat beyond a selected preset amount in a given period of time.

An impedance cardiograph unit is shown generally at 22, including the appropriate transducers to be attached to the body of the patient whose heart 11 is being treated. Such an impedance cardiograph unit is manufactured by Instrumentation For Medicine, Inc., of Greenwich, Conn., described in U.S. Pat. No. 3,340,867. Impedance unit 22 provides as an output a beat-by-beat indication of blood flow through the heart, which output is coupled to a processor unit 23. Processor 23 provides at output 24 an indication of an integral of this beat-by-beat flow as total flow volume over a predetermined period of time. Output 26 from processor 23 is the beat-by-beat flow information from impedance unit 22. The outputs 24 and 26 from processor 23 are coupled to correlator 17 for use together with output 21.

An additional indication of the condition of heart 11 is provided by ultrasonic scan probe 27 coupled to ultrasonic visualization unit 28. The scan probe 27 is positioned adjacent transducer 13 on the chest of the patient in a location which does not interfere with the positioning of transducer 13. Probe 27 includes an ultrasonic transducer aimed to receive echoes of its ultrasound energy along a line through infarcted area 12 to detect motion or lack of motion of this portion of heart 11. Ultrasonic visualization unit 28 includes the necessary electronics to produce a standard M-mode display on a line through heart 11. The scanning information from probe 27 therefore provides a visual display for the physician of the condition of heart 11. In addition, the scanning information is coupled to processor 29 which is adapted to detect variations or abnormalities in motion of the heart and produces an error signal on its output 31 if, for example, movement of the viewed area of heart 11 ceases or decreases.

An additional chemical indication of the extent of damaged to heart 11 may be provided through an invasive monitoring means, as opposed to the previously discussed noninvasive monitors. If an intravenous input is established for the patient, an occasional sampling of blood may be obtained through this existing connection. The blood sample may be checked for the 5th isoenzyme of LDH, lastic dehydrogenase. It has been found that this isoenzyme provides an indication of the extent of damage to an infarcted heart. The analysis of the blood may be processed by processor 33 which provides an indication at its output 34 for the physician's use in determining the overall progress of the treatment.

Other monitoring means, both invasive and noninvasive, are available to the physician in order to determine the progress of the ultrasound treatment. Such monitoring means include analysis of the electrocardiogram R wave, analysis of the oxygen content of the blood such as through the use of a photocell and light source directed through the ear lobe of the patient, movement of the patient, and respiration of the patient.

Various outputs from the monitoring systems of FIG. 1 are coupled to correlator 17, which controls the ultrasound treatment as determined by the physician. Correlator 17 includes means for comparing the data from the minitors with the preset limits of the various monitor parameters. These limits are set by the physician and the correlator is programed to apply a programed ultrasound dosage to heart 11 of the patient should a parameter, or combination of parameters, exceed the preset tolerances. The tolerable limits for the various outputs of the monitors are set by the physician for the individual patient under treatment. The physician is also provided with available settings at correlator 17 to program ultrasound treatment when a combination of output conditions exist at two or more monitors, perhaps even though neither monitor output is itself out of tolerance.

For example, if the number of PVC's indicated on output 21 from PVC detector 19 exceed a certain number, selected by the physician, in a predetermined period of time, correlator 17 activates timer 16, which in turn activates ultrasound unit 14 and transducer 13 to apply ultrasound to the heart 11 for the amount of time present on timer 16 for that particular condition. Simultaneously, the intensity of the ultrasound treatment is also determined by correlator 17, dependent on the out-of-tolerance monitor output, and the appropriate intensity indication is fed through control line 36 to ultrasound unit 14. Correlator 17 is also programed to provide either pulsed or continuous ultrasound dependent upon the nature of the activating monitor output. Pulsed ultrasound permits the use of higher intensities of energies while producing the same heating as a lower intensity continuous output.

As an example of the combined effect of two monitor outputs, if PVC detector indicates an elevated, though tolerable, number of premature ventricular contractions, and if impedance unit 22 indicates a somewhat lowered, though tolerable, blood flow in the heart, then processor 17 may be programed by the physician to administer a desired length and type of ultrasound treatment to the heart.

It is also obvious that the physician may, in addition to controlling the treatment regimen through computer 17, study the outputs of the monitors himself and directly activate ultrasound energy through transducer 13 in response to his determination of the significance of the viewed monitor outputs.

Figure 2:
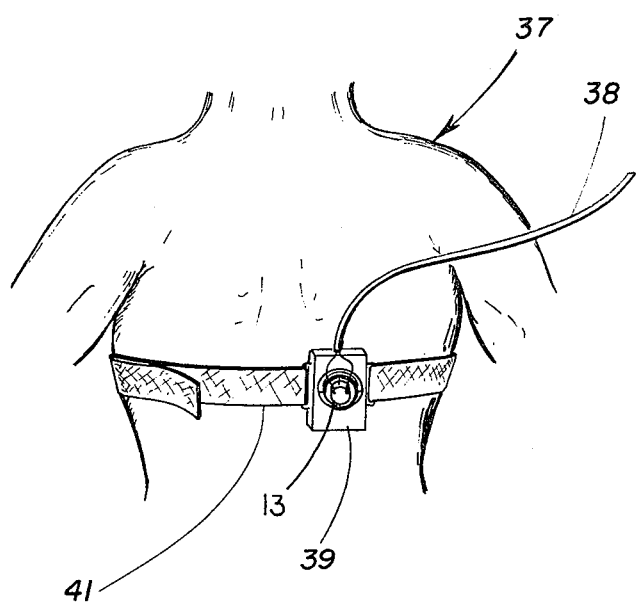
FIG. 2 is a perspective view of the attachment of an ultrasonic transducer to a patient for treatment of post-myocardial infarct.

Referring now to FIG. 2, there is shown patient 37 with transducer housing 39 fixed upon his chest by strap 41 attached to housing 39. Adjustable strap 41 encircles the patient's chest and back to maintain housing 39 in a fixed position. Transducer 13 is mounted within housing 39 and coupled through leads in cable 38 to ultrasound unit 14. Transducer 13 is aimable within housing 39 and, once aimed, may be fixed into position. Transducer 13 is gimbal-mounted in housing 39 so as to be aimable in any direction and locking means are provided to maintain the transducer in its selected orientation. An acoustic coupling gel pack is positioned between the transducer and the patient's chest for coupling the ultrasound to the patient. The various other connections, for the monitoring means such as the transducers for impedance unit 22, have not been shown in FIG. 2 for clarity.

While there have been described above the principles of this invention in connection with specified apparatus, it is to be clearly understood that this description is made only by way of example and not as a limitation in the scope of the invention.

What is claimed is:

1. Apparatus for the therapeutic application of ultrasound to a subject's heart comprising:

transducer means for producing ultrasonic energy at an output;

positioning means for directing the output of the transducer means to the heart of the subject;

monitor means for monitoring the condition of the heart, having a signal at an output dependent upon the condition of the heart;

control means, having an input and being responsive to signals at its input representative of the condition of the subject's heart, for controlling the production of ultrasonic energy by the transducer means in response to signals at its input; and feedback means for coupling the output of the monitor means to the input of the control means.

2. The apparatus of claim 1 in which the transducer means includes an ultrasonic transducer, and the positioning means includes means for monitoring the transducer on the chest of the subject whose heart is being treated, and further comprising acoustic coupling means for coupling the ultrasonic energy from the transducer to the chest of the patient.

3. The apparatus of claim 2 in which the monitor means includes premature ventricular contraction detector means having an input coupled from the subject and an output coupled to the control means, for producing at its output an electrical signal indicative of the occurrence of a premature ventricular contraction of the heart of the subject.

4. The apparatus of claim 2 in which the monitor means includes ultrasonic scan means for producing a display of the interior structure of the heart of the subject.

5. The apparatus of claim 2 in which the monitor means includes impedncc cardiograph means, coupled from the subject whose heart is being treated and having an output coupled to the input of the control means, for producing at its output an electrical signal indicative of the flow of blood through the heart of the subject.

6. The apparatus of claim 5 in which the monitor means includes premature ventricular contraction detector means having an input coupled from the subject and an output coupled to the control means, for producing at its output an electrical signal indicative of the occurrence of a premature ventricular contraction of the heart of the subject.

7. A method of applying ultrasound to the heart of a subject in the treatment of post-myocardial infarct comprising the steps of:

positioning an ultrasonic transducer near the heart of the subject such that ultrasonic energy from the transducer is acoustically coupled to the infarcted area of the heart;

monitoring the condition of the heart of the subject; and activating the transducer to produce ultrasonic energy directed to the infarcted area of the heart of the subject in response to needs indicated by said monitoring.

8. The method of claim 7 in which the monitoring step comprises detecting and indicating conditions of abnormal ventricular dynamics, and the activating step is in response to said conditions of abnormal ventricular dynamics.

9. The method of claim 7 in which the monitoring step comprises detecting and indicating conditions of reduced blood flow in the heart, and the activating step is in response to said reduced blood flow.

* * * * *